United States Patent
Wenner et al.

[11] Patent Number: 5,397,358
[45] Date of Patent: Mar. 14, 1995

[54] BONE IMPLANT

[75] Inventors: Ulrich Wenner, Uelzen; Rudolf Dierl, Dachau, both of Germany

[73] Assignee: Man Ceramics GmbH, Deggendorf, Germany

[21] Appl. No.: 645,584

[22] Filed: Jan. 24, 1991

[30] Foreign Application Priority Data

Feb. 14, 1990 [DE] Germany .................. 40 04 472.6
Feb. 14, 1990 [DE] Germany .................. 40 04 475.0

[51] Int. Cl.⁶ ............................................. A61F 2/28
[52] U.S. Cl. ......................................... 623/16; 623/23
[58] Field of Search ................ 623/11, 16, 18, 20, 623/22, 23, 66

[56] References Cited

U.S. PATENT DOCUMENTS

| 4,089,071 | 5/1978 | Kalnberz et al. | 623/16 |
| 4,892,552 | 1/1990 | Ainsworth | 623/23 |
| 4,902,297 | 2/1990 | Devanathan | 623/16 |
| 4,978,360 | 12/1990 | Devanathan | 623/66 |
| 5,181,930 | 1/1993 | Dumbleton et al. | 623/22 X |

FOREIGN PATENT DOCUMENTS

| 3243861 | 10/1983 | Germany | 623/16 |
| 3524020 | 10/1986 | Germany | 623/16 |
| 1306027 | 2/1973 | United Kingdom | 623/18 |
| 85004323 | 10/1985 | WIPO | 623/22 |
| 9015708 | 12/1990 | WIPO | 623/16 |

*Primary Examiner*—David Isabella
*Attorney, Agent, or Firm*—Ladas & Parry

[57] ABSTRACT

A bone implant is so designed that it consists of a main body, more particularly in the form of a core and unidirectional fibers, said core being surrounded by braided fiber configuration. The braided fiber configuration has an elevated fiber fraction in order to grain the surface of the braided structure. This grained surface aids the coalescent growth of natural bone tissue on the implant. The braided fiber configuration simultaneously serves as a torsion box.

12 Claims, 3 Drawing Sheets

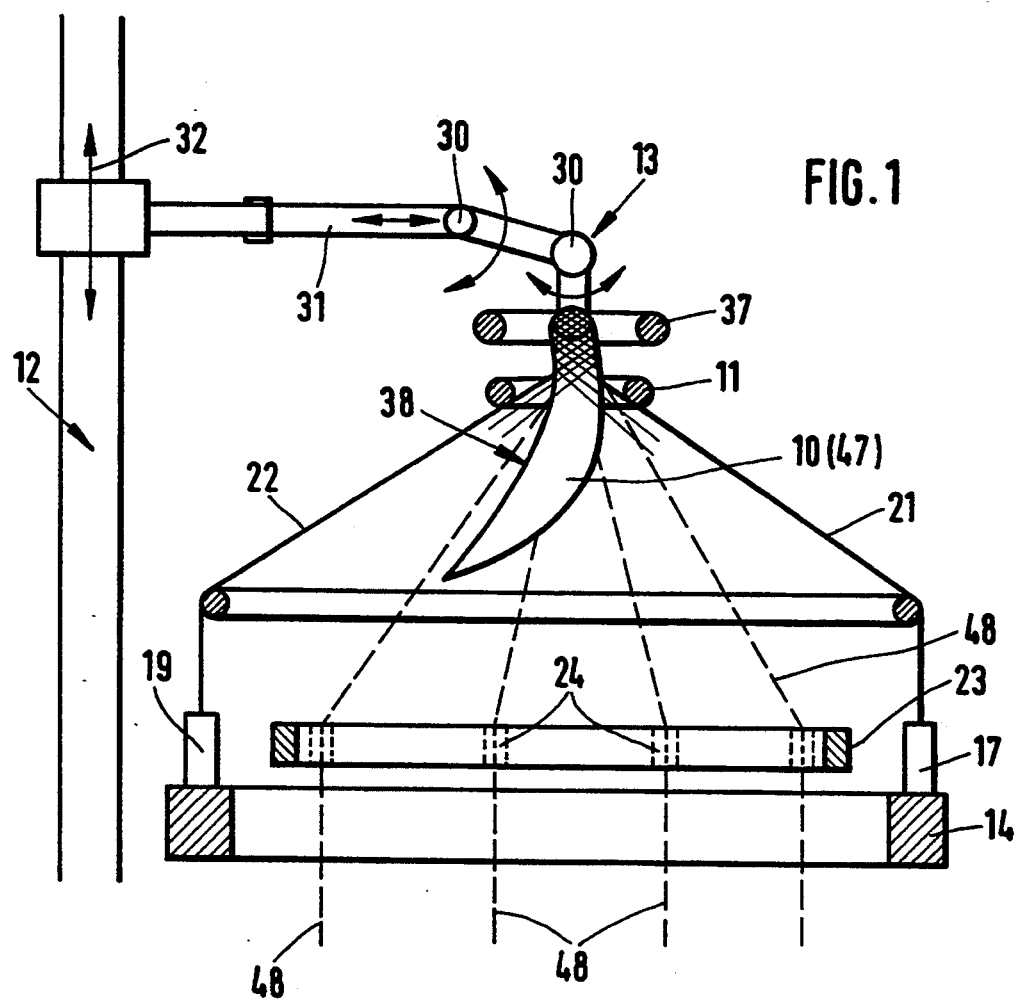
FIG. 1
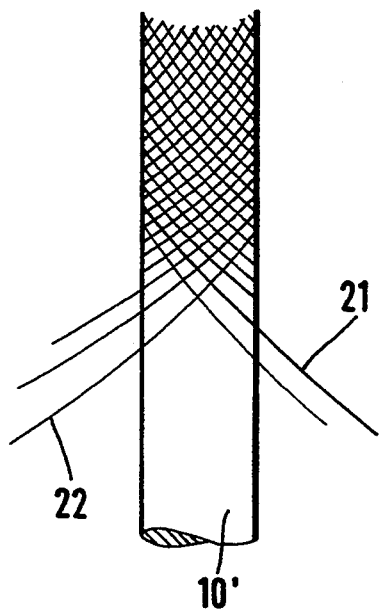
FIG. 2
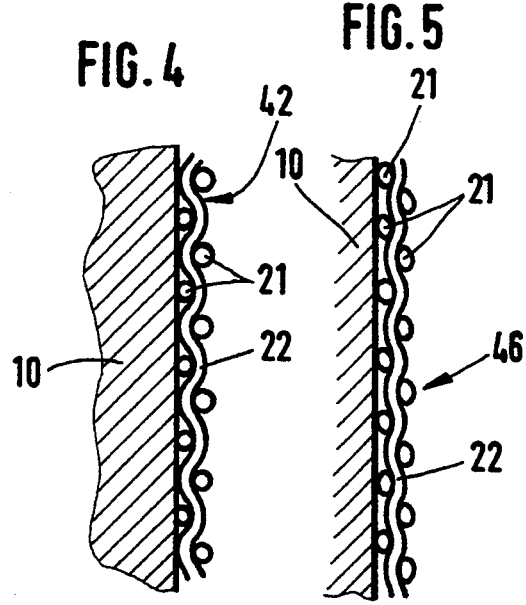
FIG. 4
FIG. 5

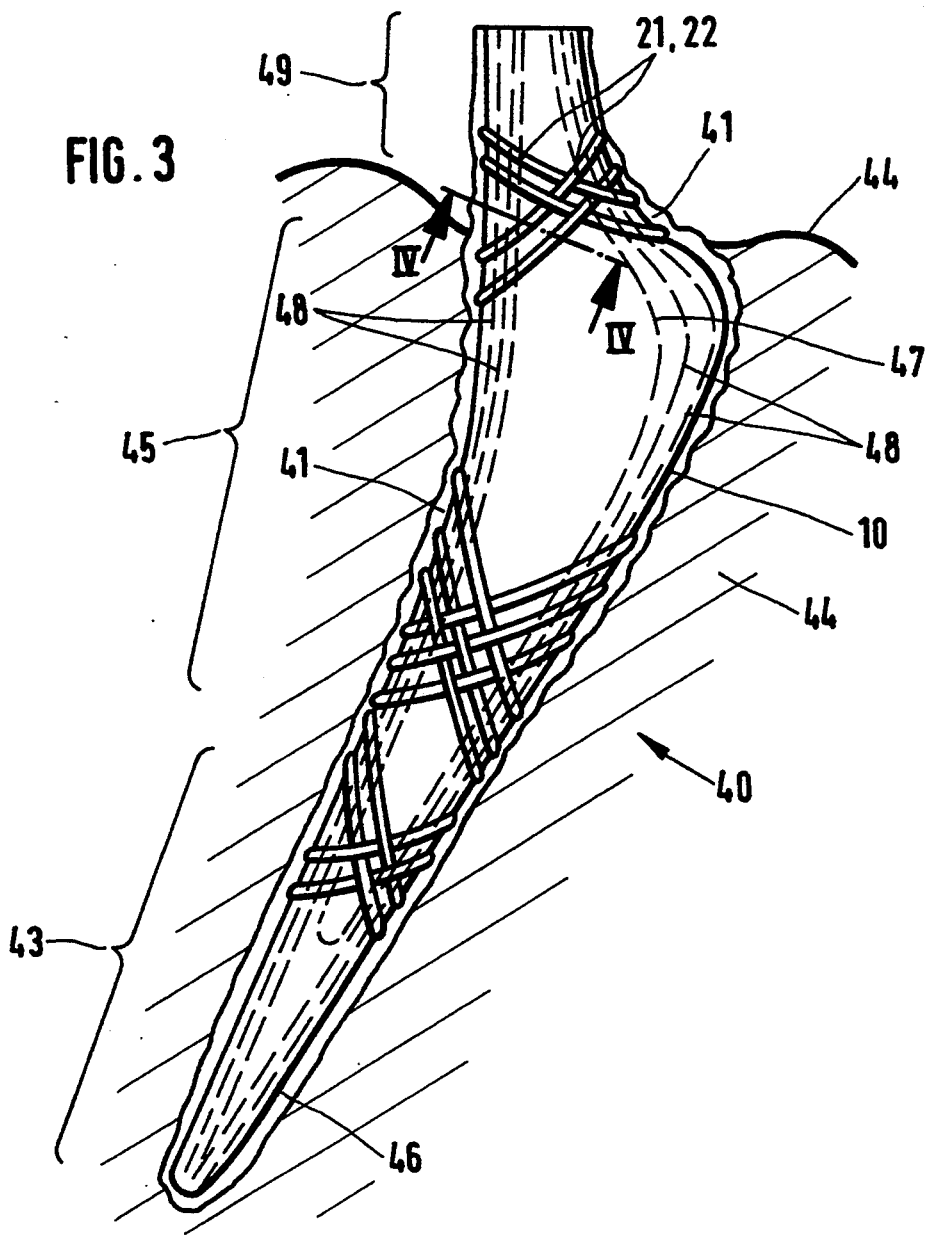

BONE IMPLANT

BACKGROUND OF THE INVENTION

The invention relates to a bone implant comprising a main body and a braided fiber array partially surrounding the main body.

An implant of this type is described in the German patent publication 3,909,545 in the form of a hip joint endoprosthesis. This known bone shank consists of an inner core, and an intermediate layer in the form of braided fibers and an injection cast outer layer defining the final form, such three components extending from the distal to the proximal end of the shank.

The implant designed in this manner with separate components is intended to adapt to the flexibility of the bone. The outer layer, which is made of polyetheretherketone is not suitable for adherent growth of the natural bone tissues thereon. It is for this reason that cushions of metal fiber are provided In the middle part of the shank, into which the bone tissue and/or a bone cement is to penetrate. In the case of such a design it is uncertain whether a movable cushion is suitable as an intermediate layer for connecting together two components.

SUMMARY OF THE INVENTION

An object of the present invention is to provide a bone Implant of the type initially mentioned so that during the growing process there is good adhesion between the implant and bone material.

In order to achieve this and/or other objects, the layer of braided fibers forms the outer layer of the implant and has a grained surface.

This grained or structured surface caused by the braided fibers ensures that the surface is suitable for the desired coalescent growth process of the bone material and has the advantage that the structure Is firmly joined to the implant and furthermore serves as a radial support for the main body, which during use has to withstand considerable loads.

The invention provides a braided configuration or structure preferably made up of tightly twisted fibers and a bonding matrix material wherein the round cross section of the fibers maintained in the braided configuration and the surface structure is reinforced.

In accordance with a further advantageous feature of the invention the braided configuration has a ms,or proportion of fibers, which may be up to 70%. Then in this manner it is possible for the surface structure which may be produced by the fibers to remain unchanged, that is to say the depressions are not filled with matrix material. In the case of a matrix material fraction of only 30%. It Is possible to ensure that on the one hand the fibers enter into a strong bond with themselves and with the core and on the other hand there is no excess matrix material. The main body may have any acceptable shape and may consist of any material which has proved successful.

The braided fiber configuration however has a particularly beneficial effect in conjunction with a main body which predominantly consists of unidirectional fibers, that is to say fibers in alignment with the longitudinal direction of the shank. Owing to the change in the cross section such a shank has a core acting as a displacing body in its interior. Such a main body has an optimum design for receiving and transmitting on the loads acting on the prosthesis shank, more particularly in the form of thrusts. Simply owing to the added braided structure there is an increase in the properties, because the braided structure serving as a means aiding coalescent growth is able to take up radial and torsional forces. Such a shank is furthermore simple to produce and is suitable for mass production.

In the case of such an implant the casing forms the body actually taking up and transmitting forces. For this purpose the fibers in longitudinal alignment in accordance with an earlier proposal in their totality extend from one end to the other of the shank. Owing to irregular geometry of the shank an inner core is necessary, which within the casing serves as a displacing body. It is In this manner that optimum use is made of the fibers since all the fibers making up the forces contribute to the transfer of the forces to other parts of the shank. The conduction of the forces is kept in the casing, that is to say on surface of the shank and, respectively, in the vicinity of the surrounding bone material in the implanted state. Accordingly the forces are transferred directly via the fibers to the coalescing bone zone or possibly to an intermediately placed adhesive material. These forces are mostly thrusts acting in the longitudinal direction of the shank.

As part of a further advantageous feature of the present invention the casing is pervaded by at least one braided fiber configuration, this resisting undue bending due to bending forces, which act in the shank owing to motion.

The braided fiber configurations offer an optimum radial support for the unidirectional fibers of the casing. The braided fibers mutually act to provide stability and strength owing to the direction of braiding and maintain their original positions, this being more particularly significant in the convex part of the curved shank which is most heavily stressed. The radially supporting fibers are therefore not able to be laterally detached as in the case of oblique fibers, or fibers extending in the circumferential direction as applied by known winding methods The inner braided structure means additionally that there is opposition to any lateral shift of the unidirectional fibers in the convex zone since the unidirectional fibers on the one hand are split up into zones and on the other hand the contact interface between the unidirectional fibers and the grained surface of the braided structure is increased which tend to anchor the unidirectional fibers in their original position. The two braided structures form a sort to twin torsion box, which in conjunction with the unidirectional fibers are responsible for optimum stiffness of the shank in relation to all forces occurring.

Since the structured or grained character of the fibers in the braided structure somewhat interferes with a strictly regular or rigid state of the directly adjacent unidirectional fibers, it is an advantage that the major part of the unidirectional fibers forms the inner casing layer, while it is only a residual part of approximately 30% that takes up a position between the braided structures. In the case of a larger number of unidirectional fiber layers it is possible for the fraction between the two braided structures to be increased up to a maximum value of 50%.

The fibers of the braided fiber configuration preferably have an orientation of $\pm 45°$ along the entire length of the shank.

The invention furthermore relates to a method of producing a bone implant in which the braided structure Is produced by means of a braiding machine maintaining an even tension in the fibers, the main body being rocked during the braiding operation in order to produce the desired orientation of the braided fibers.

The prefabricated main body forms the actual shank which is more particularly adapted to withstand axial thrusts. The main body is a composite structure and more particularly a fiber composite body or a component, which with respect to its material is homogeneous, onto which the fibers are directly braided. This ensures that the fibers have the same tension over the entire component despite the irregular configuration. The rocking of the main body during the braiding operation determines the orientation of the fibers over the full shank. In this respect the orientation may be kept constant along the length of the shank or it may be varied in accordance with desired criteria. The rocking and feed motion of the main body takes place in accordance with the desired orientation. It is important that simultaneously the fiber tension, which is determined by the braking action of the fiber guide and the feed rate of the main body, may be affected in a controlled manner. This applies both for the inner braided structure or structures and also for the outer braided structure.

In the case of a composite fiber shank the outer braided structure not only serves as an aid for coalescing growth but also, as in any inner braided structures, a torsion box or, respectively, radial support for the fiber layers contained in the main body. The combination of inner longitudinally directed unidirectional fibers with an outer braided fiber configuration represents a shank which is advantageous as regards manufacturing technology, and which has optimum mechanical properties for use as part of a hip joint endoprosthesis, this being furthermore made possible by the use of carbon fibers. Carbon fibers have not only favorable strength properties but are also tissue-compatible.

For the mass production of such shanks it is possible to use a supporting core which is placed on a braiding machine in which the unidirectional fibers are simultaneously applied to the support core with the braid fibers.

For the operation of making the outer braided layer pre-twisted fibers are preferably used, which have a twist rate of up to 30 twists per meter. Such fibers substantially maintain their round cross section in the braided structure even if the same was produced with fibers held under high tension.

In accordance with a further particularly useful feature of the invention the braided fiber configuration has a low fraction of matrix. This is made possible by using a highly diluted matrix material for instance diluted with acetone.

In accordance with a further advantageous feature of the invention the main body is coated with resin prior to the application of the braided structure, such resin being applied by brushing, by immersion dipping or the like. Furthermore it is possible to use diluted resin. Accordingly the resin fraction in the fibers used for bonding together the individual filaments of a fiber may be kept to a minimum, while the bond to the main body is due to the matrix material applied to the main body. Thus it is possible to positively ensure that there is no excess of matrix material smoothing over the surface of the braided structure.

If it is desired to preclude coalescent bone growth in one zone of an implant, then in accordance with a further feature of the invention the zone is subjected to a treatment with heat and pressure in which the surface of the respective zone is flattened by forming.

In the case of a shank for a hip joint implant for instance the proximal end of the shank, which is introduced into the femur, is preferably treated in this manner in order to limit the coalescent growth zone to the upper end of the shank inserted into the femur, more particularly if the shank does not attain the flexural elasticity of the bone.

However furthermore it is possible in such cases to only provide the implant with a braided structure in those parts in which there is to be coalescent growth with the bone material.

In the case of the use of biocompatible fibers such as for instance, carbon fibers, it is readily possible to lay bare the fibers on the surface by using a mechanical method later without damaging the fibers. This may be performed for instance by brushing with special brushes or by blasting with sand or carborundum.

Further features and advantages of the invention will be gathered from the ensuing detailed description of two embodiments thereof referring to the drawings.

BRIEF DESCRIPTION OF THE DRAWINGS

FIG. 1 is a schematic diagram of an apparatus for producing the bone implant of the present invention;

FIG. 2 shows the application of fibers to the main body in a braided configuration;

FIG. 3 is a side view of the bone implant of the present invention implanted into bone material;

FIG. 4 is a partial cross sectional view taken along line IV—IV in FIG. 3;

FIG. 5 is a cross sectional view of the present invention showing the braided fiber configuration in a flattened shape;

DETAILED DESCRIPTION OF THE PREFERRED EMBODIMENT

Figure 6:
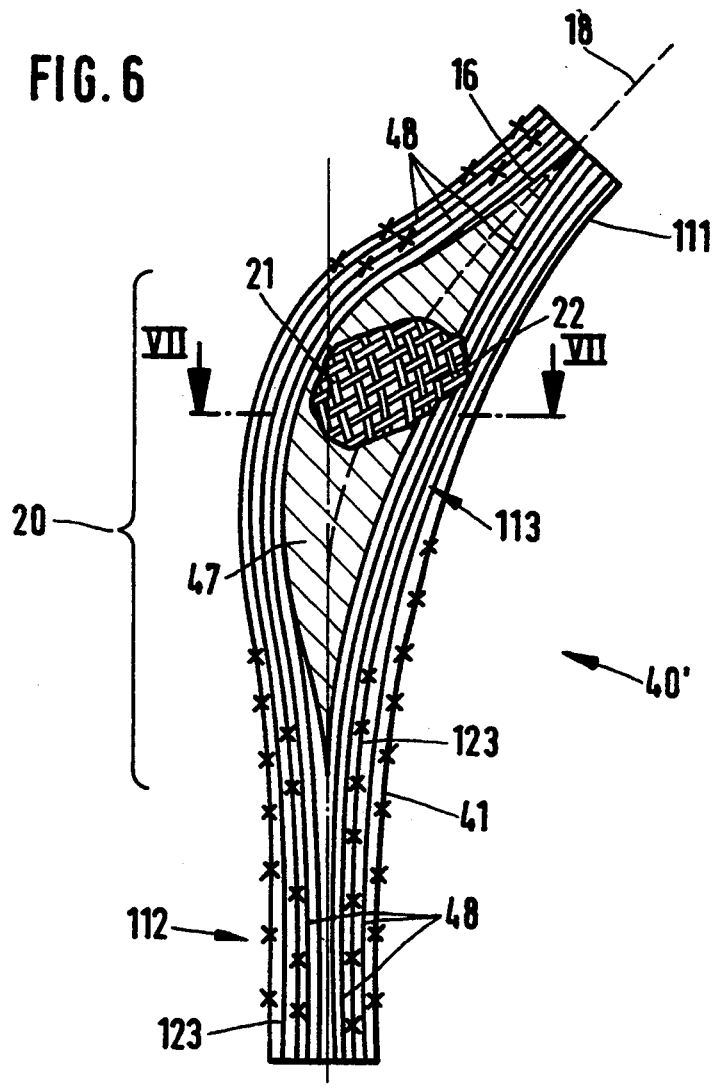
FIG. 6 is a cross-sectional side view of a second embodiment of the present invention.
Figure 7:
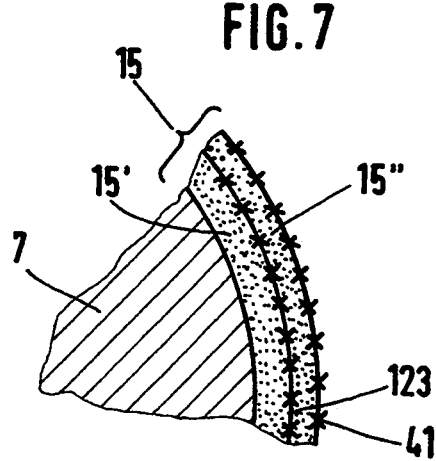
FIG. 7 is a partial cross sectional view taken along line VII—VII in FIG. 6.

FIG. 1 shows an arrangement for the production of the shank of an endoprosthesis starting from a prefabricated main body 10. The main body is drawn through the fiber eye of a conventional braiding machine 12 by means of a gripper 13. The braiding machine 12 has as its main part a guide ring 14, on which two sinusoidal guide rails, not illustrated, for a given number of fiber bobbins 17 and, respectively, 19 are provided, which are placed in two groups and are moved In opposite direction in the guide rails.

At the start of the braiding operation all ends of the fibers 21 and 22 are connected with the gripper 13, which simultaneously bears the core and moves with it at a given speed away from the fiber eye 11. For curved or otherwise irregular implants 40 as is the case with the endoprosthesis shank illustrated in FIG. 3, the gripper 13 is equipped with joints 30, telescoping means 31 or the like in order to be able to perform a rocking motion in addition to the feed motion 32. Accordingly the component may be so aligned that the fibers 21 and 22 have the desired orientation in the respective zone of the implant.

Owing to the motion of the fiber bobbins 17 and, respectively, 19 in the guide rails the individual braid fibers describe oppositely running helices during the course of the braiding process, as they are illustrated in FIG. 2 with reference to a simple cylindrical component 10', each individual fiber 22 being placed alternately under and over other fibers 21, as shown in FIG. 4.

The helix angle of the wound braiding fibers and, respectively, their orientation on the eventual component are set by the speed and the setting of the main body 10 as it is moved through the fiber guide eye 11, the condition of the braiding machine 12 and the respective cross section of the main body 10 playing a part as well. By suitable programming of the gripper driving mechanism it is possible to automate a change in the feed speed and of the rocking action in accordance with the geometry and, respectively, the cross section of the main body 10 so that every part of the main body has an orientation of the braided fibers 21 and 22 which is desired in the given zone.

A further parameter is the number of fibers 21 and 22 and it is dependent on the dimension of the component to be produced and the desired density of the braided structure for a given orientation of the fiber. For a shank for hip joint implants 20 to 40 fiber strands 21 and 22 are used for a setting at approximately 45°.

For braiding around a main body 10 the latter is coated with matrix material by dipping impregnation, brushing or the like, and together with the fiber ends secured to the gripper 13. The gripper 13 is moved at a set speed, which in some cases may vary during the course of the braiding process, its angular setting being changed in accordance with the curvature of the main body 10. The desired fiber tension—for instance 350 g—is produced by the braking action of the fiber bobbins 17 and 19.

The fibers 21 and 22 are respectively passed through impregnating devices, not illustrated, in which a highly diluted matrix material is contained, using for instance acetone as a diluent.

The degree of dilution is so selected that the fraction of the resin still remaining on the finished component after evaporation of the diluent is just sufficient to connect the individual filaments of the respective fibers, to connect the fibers themselves together and to connect the fibers with the main body so that there is essentially no surplus resin. The connection of the fibers with the main body 10 is aided by the matrix material applied to the main body 10.

This method endows the surface of the finished implant 40 with the structure or grain of the braided fiber, which is coated with a very thin and even layer of matrix material. The graining effect may be made more pronounced by the use of intensely twisted fibers 21 and 22. For this purpose suitably twisted fibers are wound on the fiber bobbins 17 and 19, the direction of twist having to be opposite in the case of the two bobbin groups 17 and 19 in order to ensure that the fibers are not untwisted during the braiding operation. The degree of twist is preferably empirically ascertained. In the case of carbon fibers a twist rate of up to 30 twists a meter has turned out to be satisfactory. The twisted together fibers 21 and 22 cause the braided fibers to keep their round cross section so that the surface grain is enhanced, as shown in FIG. 4.

Owing to the use of a minor fraction of matrix material the fibers 21 and 22 are only coated with a thin matrix film, whose thickness is essentially even, that is to say the depressions 42 are not deepened, over the entire surface. This means that the natural grain of the braided fibers is maintained. Accordingly it is possible furthermore to remove the matrix film over the entire surface of the braided structure 41 and to expose the fibers without damaging the fibers 21 and 22. This is more particularly so in cases in which the biocompatibility of the fibers 21 and 22 used is superior to that of the matrix material.

The method as described above is able to be used for mass production of implants made of braided structures comprised of braided fibers and coatings. The braided structure produced directly on the main body furthermore makes possible the design of implants able to be produced in an extremely simple way with optimum mechanical properties. The braided fiber configuration, which serves to promote coalescent growth, when arranged with a suitable orientation of approximately ±45° and when using high tensile fibers, such as carbon fibers, withstands torsion and radial loads. With an inner layer of fibers with an orientation of 0°, the loading configuration is completed, since these unidirectional fibers in alignment with the longitudinal direction of the shank take up the thrust and tension loads and are radially supported by the braided structure. Owing to the varying cross sections of the shank it is not possible for the longitudinally directed fibers, whose overall cross section is set by the thinner end (this being the upper or lower end) of the shank, to fill up the shank in the thicker middle part. Here a core is used, which preferably consists of short fibers, as a displacing or filling body. It has been seen that a shank with such a structure is able to withstand the loads in the implanted condition excellently and permanently and transfer such loads to the surrounding bone.

The production of the implant may take place in simply two method steps, in which in the first step the core is suitably produced in a manner suited to the material of which it is made. In the case of a composite fiber core pressing will be the most suitable method. In the second step the core is united with the longitudinally directed fibers and also with the braided fibers. For this purpose the braiding machine 12 is equipped with a further fiber guide ring 23 through whose fiber eyes 24 fibers 48 are drawn for the unidirectional plies or layers. These fibers 48 are drawn together with the braiding fibers 21 and 22 in one working step and applied to the core 47. In this case the core 47 takes the place of the main body 10.

As shown in FIG. 3 a completed shank 40 for a hip joint endoprosthesis consists of the inner core 47, the unidirectional fibers 48 and the tube or hose 41 composed of braided structure. The core 47 fills the inner cavity of the zone 45 of the maximum cross section of the shank 40. The proximal end 43 consists completely of unidirectional fibers 48 and the surrounding braided structure.

In the case of a hip joint it is an advantage if the proximal end 43 of the same remains free in the bone material 44 in order to allow for the differences in stiffness between the bone 44 and the implant 40. In this case the surface of the proximal end 43 is preferably manufactured without any grain. In the case of a main body 10 of homogeneous material this is for instance possible if it is only in the coalescent growth area 45 that a braided structure 41 is applied to the implant.

In the case of a composite fiber shank and more particularly in the case of a main body consisting of a core 48 and unidirectional fibers, the entire main body 10 is to be coated with the tube or hose braided structure or hose 41 serving simultaneously as a torsion box. Maximum smoothness of the surface at the proximal end 43 is then achieved if the implant 40, on which braiding has been completed, has its respective end 43 subjected to heat and pressure, during which treatment the fibers 21 and 22 as shown in FIG. 5 are flattened so that in region 46 the braided structure looses its surface grain more or less completely. The same operation is performed at the other end 49, on which a femur condyle or joint ball (not illustrated) is mounted. The complete composite fiber shank may consist of a fiber material and a matrix material.

FIG. 6 shows a longitudinal section of a shank 40' hip joint endoprostheses, which has an essentially cylindrical upper end 111 in order to receive a femur condyle, not illustrated, a lower end 112 and a curved middle part 113, which is widened in its cross section. The shank 40' is essentially manufactured of unidirectional fibers 48, which extend in the longitudinal direction of the shank 40' from the one end 113 as far as the other end 112 of the shank 40'.

Owing to the widening of the cross section in the middle part 113 and to the greater cross section of the upper end 111, the unidirectional fibers 48 form a casing 15 in the middle part, while at the upper end 11 they leave a fine channel 16. The cavity between the unidirectional fibers 48 is filled by a core 47 so as to leave no gaps, such core being able to withstand inwardly directed radial forces.

In order to be able to withstand outwardly directed radial forces, which occur more particularly In the convex arch part 20, the shank 40' has at least one further braided structure 118 in addition to the outer braided structure 41. The inner ply 123 of braided fibers is positioned between the unidirectional fiber plies in such a manner that the casing 15 is split up into two plies or, respectively, ply groups 15' and 15". This second, inner braided structure 23 supports the action of the outer braided structure 41. As shown in FIG. 6 in the form of a partial plan view of the outer braided structure 41, the fibers 21 extend in one direction alternately under and over the fibers 22 running in the transverse direction, a grained surface structure being produced on either side of a braided structure 41 and, respectively, 123. This surface grain simultaneously enables tangential anchoring, at least of the unidirectional fibers 48 adjoining the braided structures, This effect as well is reinforced by the splitting up of the braided structure into two plies 41 and 123, which are not directly in contact with each other.

However on the other side the configuration of the unidirectional fibers in the interface of the braided structures 41 and 123 is affected by the graining of the surface so that the stress therein decreases slightly. In order to minimize this effect, the inner braided structure 123 is so positioned in the radial direction that in the inner zone, that is to say he zone 15' adjacent to the core 47, the greater part of the unidirectional fibers 48 is to be found. This fraction of the fibers will be dependent on the number of the plies 48 of unidirectional fibers and amounts to between 50 and 90% of the total amount of unidirectional fibers.

We claim:

1. A bone implant of curved, irregular shape comprising a main body and a braided fiber structure on said main body constituting an outer layer of the implant, said braided fiber structure comprising a plurality of fibers wound over and under one another on said main body, each fiber being tightly twisted along a length of the fiber to produce a substantially circular cross-section of said fibers in the braided fiber structure and provide an irregular outer surface for the braided fiber structure which will facilitate intergrowth with bone material, said main body having an irregular cross-section related to the curved irregular shape of the bone implant so that when said fibers of said braided fiber structure are applied to said main body said braided fiber structure provides the finished curved, irregular shape of the bone implant and said outer layer thereof, said braided fiber structure further comprising a matrix material binding said fibers to one another and to said main body, said fibers being present in said braided fiber structure in an amount of 70% and said matrix material in an amount of 30%.

2. The implant according to claim 1, wherein the main body comprises a core member and an inner layer of fibers applied to said core member so that said fibers of said inner layer are aligned with a longitudinal axis of the core member.

3. The implant according to claim 1, wherein the main body consists of composite fiber material.

4. The implant according to claim 3, wherein the main body and the fibers of the braided fiber structure are made of the same material.

5. The implant according to claim 1, comprising a plurality of layers interposed between said braided fiber structure and said main body comprising a first layer on said main body including fibers aligned with a longitudinal axis of said main body, a second layer including fibers wound in a braided configuration on said first layer, and a third layer of fibers aligned with the longitudinal axis of the main body.

6. The implant according to claim 5, wherein the fibers in the braided fiber structure have an angle of ±45° relative to said longitudinal axis.

7. The implant according to claim 6 wherein the fibers of said first layer constitute 50 to 90% of the longitudinal aligned fibers of said first and third layers and the fibers of said third layer constitute 10 to 50% of said longitudinal aligned fibers.

8. A bone implant according to claim 1, wherein said fibers are a major constituent of said braided fiber structure and said matrix material is a minor constituent thereof so that the matrix material does not substantially alter said irregular outer surface of the braided fiber structure.

9. A bone implant as claimed in claim 8, wherein said matrix material is embedded in said fibers of said braided fiber structure.

10. A bone implant as claimed in claim 8 wherein said matrix material is as a thin layer applied to said main body, said fibers penetrating into thin layer.

11. A bone implant of curved, irregular shape comprising a main body and a braided fiber structure on said main body constituting an outer layer of the implant, said braided fiber structure comprising a plurality of fibers wound over and under one another on said main body, and a matrix material binding said fibers together, each fiber being tightly twisted along a length of the fiber to produce a substantially circular cross-section of said fibers in the braided fiber structure and provide an irregular outer surface for the braided fiber structure which will facilitate intergrowth with bone material, said main body having an irregular cross-section related to the curved irregular shape of the bone implant so that when said braided fiber structure is applied to said main body said braided fiber structure provides the finished curved, irregular shape of the bone implant and said outer layer thereof, a second layer of fibers applied beneath the braided fiber structure, said fibers of said second layer being aligned with a longitudinal axis of the main body, and a second braided fiber structure beneath said fibers of said second layer.

12. A bone implant of curved, irregular shape comprising a main body and a braided fiber structure on said main body constituting an outer layer of the implant, said braided fiber structure comprising a plurality of fibers wound over and under one another on said main body, each fiber being tightly twisted along a length of the fiber to, produce a substantially circular cross-section of said fibers in the braided fiber structure and provide an irregular outer surface for the braided fiber structure which will facilitate intergrowth with bone material, said main body having an irregular cross-section related to the curved irregular shape of the bone implant so that when said braided fiber structure is applied to said main body said braided fiber structure provides the finished curved, irregular shape of the bone implant and said outer layer thereof, said braided fiber structure further comprising a matrix material binding said fibers to one another and to said main body, said fibers being-present in said braided fiber structure in an amount of 70% and said matrix material in an amount of 30%, said fibers of the braided fiber structure being oriented at an angle of ±45° with respect to a longitudinal axis of the main body.

* * * * *